US012590276B2

(12) United States Patent
Han et al.

(10) Patent No.: US 12,590,276 B2
(45) Date of Patent: Mar. 31, 2026

(54) CELL CULTURE DEVICE

(71) Applicant: AMOGREENTECH CO., LTD.,
Gimpo-si (KR)

(72) Inventors: Kyoung Ku Han, Gimpo-si (KR); **Seon
Ho Jang, Gimpo-si (KR); Jae Kyung
Song, Gimpo-si (KR); Hee Sung Park**,
Gimpo-si (KR)

(73) Assignee: AMOGREENTECH CO., LTD.,
Gimpo-si (KR)

( * ) Notice: Subject to any disclaimer, the term of this
patent is extended or adjusted under 35
U.S.C. 154(b) by 614 days.

(21) Appl. No.: 18/011,269

(22) PCT Filed: Jun. 9, 2021

(86) PCT No.: PCT/KR2021/007191
§ 371 (c)(1),
(2) Date: Dec. 19, 2022

(87) PCT Pub. No.: WO2021/256768
PCT Pub. Date: Dec. 23, 2021

(65) Prior Publication Data
US 2023/0227761 A1     Jul. 20, 2023

(30) Foreign Application Priority Data
Jun. 19, 2020     (KR) ........................ 10-2020-0074856

(51) Int. Cl.
*C12M 1/24*          (2006.01)
*C12M 1/00*          (2006.01)
          (Continued)

(52) U.S. Cl.
CPC ............ *C12M 23/08* (2013.01); *C12M 23/20*
(2013.01); *C12M 23/38* (2013.01); *C12M
25/04* (2013.01); *C12M 33/14* (2013.01)

(58) Field of Classification Search
CPC ...... C12M 23/08; C12M 23/20; C12M 23/38;
C12M 25/04; C12M 33/14
(Continued)

(56) References Cited

U.S. PATENT DOCUMENTS

| | | | |
|---|---|---|---|
| 9,708,576 B2 * | 7/2017 | Seippel ................. | C12M 23/02 |
| 2014/0057346 A1 | 2/2014 | Johnson | |
| 2020/0179923 A1 * | 6/2020 | Lacey .................... | C12M 23/20 |

FOREIGN PATENT DOCUMENTS

| | | | |
|---|---|---|---|
| JP | 2013099282 A | * | 5/2013 |
| JP | 2014-168402 A | | 9/2014 |

(Continued)

OTHER PUBLICATIONS

JP-2013099282-A Machine English Translation (Year: 2013).*
(Continued)

*Primary Examiner* — Michael L Hobbs
*Assistant Examiner* — Lenora A Abel
(74) *Attorney, Agent, or Firm* — Schmeiser, Olsen &
Watts LLP

(57) ABSTRACT

A cell culture device is provided. A cell culture device
according to an exemplary embodiment of the present
invention includes: a main body comprising a culture space
having one surface that is open; and a surface-modified
sheet-type culture plate which is fixed to the main body to
cover the opened one surface of the culture space, and thus
forms a culture surface on which cells are cultured, and
which forms the culture surface so that the cells can be
attached to the culture surface.

8 Claims, 6 Drawing Sheets

(51) Int. Cl.
     *C12M 1/12*          (2006.01)
     *C12M 1/26*          (2006.01)
(58) Field of Classification Search
     USPC ........................................................ 435/304.3
     See application file for complete search history.

(56)                 References Cited

FOREIGN PATENT DOCUMENTS

| | | | |
|---|---|---|---|
| JP | 2015221002 | A | 12/2015 |
| KR | 10-2015-0111535 | A | 10/2015 |
| KR | 10-2017-0063015 | A | 6/2017 |
| KR | 20170140785 | A | 12/2017 |
| KR | 10-2020-0056331 | A | 5/2020 |
| WO | 2011/093342 | A1 | 8/2011 |

OTHER PUBLICATIONS

International Search Report for PCT/KR2021/007192 mailed Oct. 8, 2021.
International Search Report for PCT/KR2021/007191 mailed Oct. 8, 2021.

* cited by examiner

CELL CULTURE DEVICE

CROSS-REFERENCE TO RELATED APPLICATIONS

This application claims priority to PCT/KR2021/007191, having a filing date of Jun. 9, 2021, which claims priority to Korean Patent Application No. 10-2020-0074856, having a filing date of Jun. 19, 2020, the entire contents both of which are hereby incorporated by reference.

FIELD OF TECHNOLOGY

The following relates to a cell culture device.

BACKGROUND

Cell culture is a method of culturing or proliferating cells by removing a tissue piece from an individual of a multicellular organism and then supplying nutrients to the removed tissue piece in a culture vessel.

Animal cells derived from human or animal tissues may be cultured while floating in a medium or adhering to a carrier. Floating cells can proliferate even when the cells are alone suspended in a medium, whereas adherent cells can proliferate only in a state attached to a culture surface such as a support.

Accordingly, in order to cultivate the adherent cells using a cell culture device, the adherent cells must be smoothly attached to the culture surface of the cell culture device. To this end, in cell culture using a conventional cell culture device, a coating solution is first injected into the cell culture device to modify the culture surface of the cell culture device, and then the culture surface coated with the coating solution is dried for a certain period of time. Then, the excess coating solution remaining on the culture surface is removed by a cleaning process in which a separate cleaning solution is injected into the cell culture device again.

Therefore, in the culturing of adherent cells using the conventional cell culture device, a seeding operation for attaching the cells to the culture surface must be accompanied by the operation for modifying and washing the culture surface, which is very cumbersome.

SUMMARY

An aspect relates to a cell culture device capable of facilitating the seeding operation of adherent cells while maintaining mass productivity.

In order to solve the above problems, embodiments of the present invention provide a cell culture device comprising: a body including a culture space with one side open; and a sheet-shaped culture plate fixed to the body to cover the open side of the culture space and forming a culture surface on which cells are cultured, wherein the surface of the culture plate forming the culture surface is modified so that the cells can smoothly adhere to the culture surface.

As an example, the culture plate may include a sheet-shaped nanofiber membrane coated with a motif, and a support member attached to one surface of the nanofiber membrane via an adhesive layer so as to support the nanofiber membrane, wherein an exposed surface of the nanofiber membrane may form the culture surface.

In this case, the culture plate may be formed such that the sheet-shaped nanofiber membrane has a smaller area than the support member; and the support member may include a fusion surface formed on one surface to surround an edge of the nanofiber membrane, wherein the fusion surface may be in direct contact with the body and fixed thereto.

In addition, the body may include at least one fusion mount protruding outward at a certain height along an open edge thereof, wherein the fusion mount may be fused with the fusion surface of the support member to fix the culture plate to the body.

As another example, the culture plate may be a sheet-shaped film member treated with plasma, wherein one surface of the film member may form the culture surface.

Further, the culture plate may be made of a non-toxic material.

In addition, the culture plate may further include a release film laminated on one surface thereof.

In this case, the release film may be removed after the surface modification treatment of the culture plate is completed.

In addition, the cell culture device may further include an inlet formed on one side of the body to communicate with the culture space, and a cap detachably coupled to the inlet.

In addition, the cap may further include a filter member having waterproofness and breathability.

According to embodiments of the present invention, it is possible to facilitate the seeding of adherent cells while maintaining mass productivity, thereby lowering the production cost and increasing the convenience of operation for cell culture.

BRIEF DESCRIPTION

Some of the embodiments will be described in detail, with reference to the following figures, wherein like designations denote like members, wherein.

DETAILED DESCRIPTION

Figure 1:
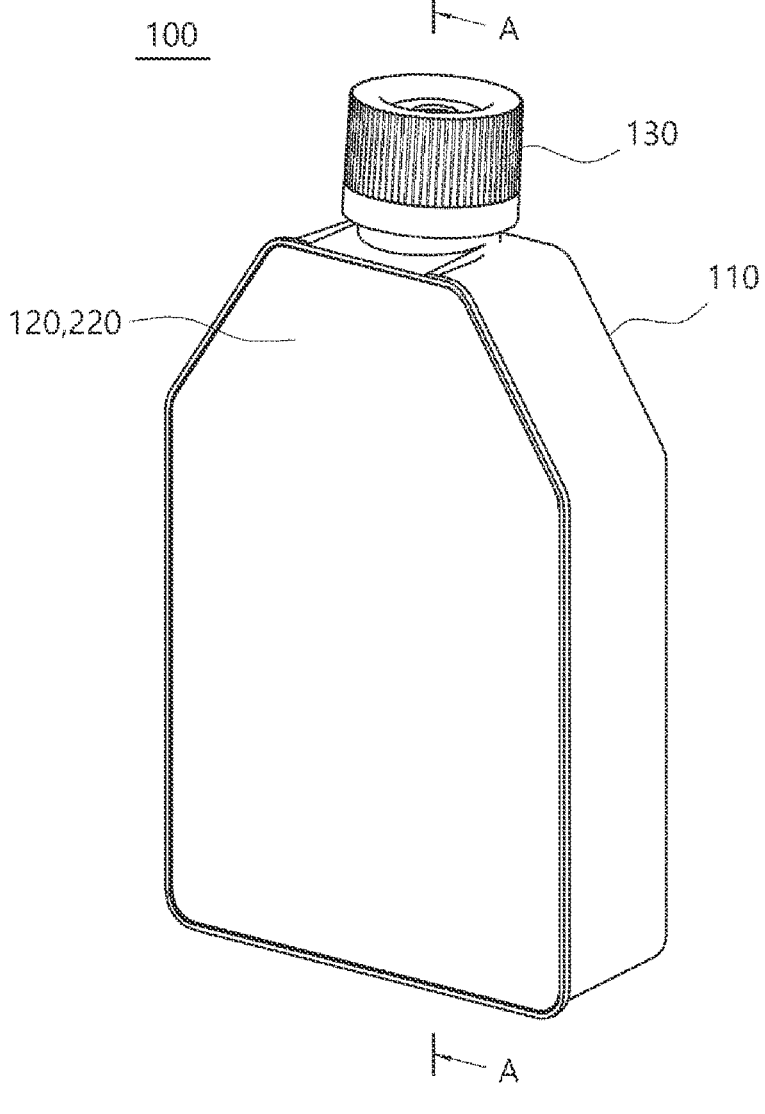
FIG. 1 shows a cell culture device according to an embodiment of the present invention.

Hereinafter, with reference to the accompanying drawings, embodiments of the present invention will be described in detail so as to be easily implemented by one of ordinary skill in the conventional art to which the present invention pertains. Embodiments of the present invention may be embodied in a variety of forms and is not be limited to the embodiments described herein. In order to clearly describe embodiments of the present invention in the drawing, parts irrelevant to the description are omitted from the drawings; and throughout the specification, same or similar components are referred to as like reference numerals.

Figure 2:
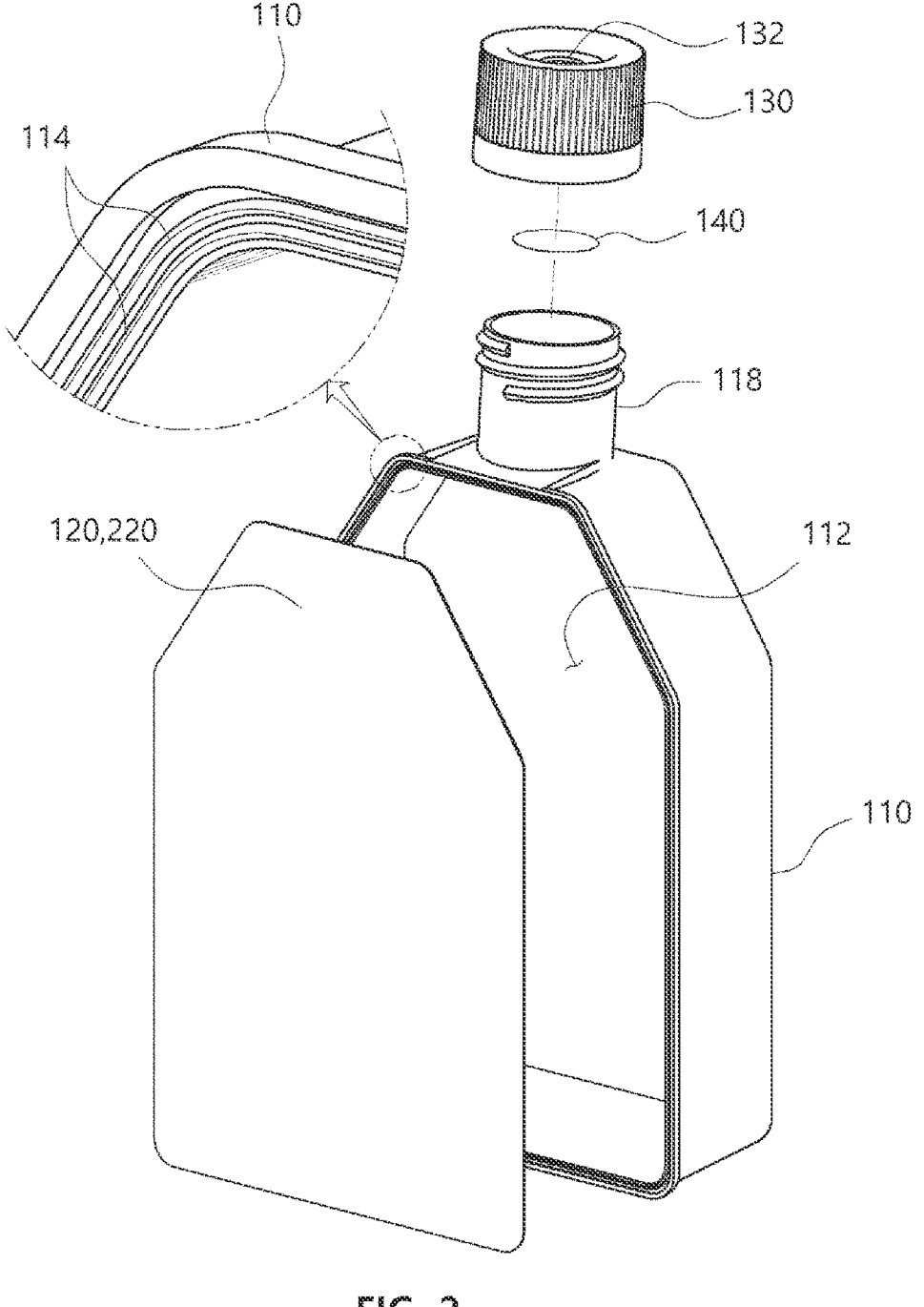
FIG. 2 shows a state in which the body and the culture plate in FIG. 1 are separated from each other.
Figure 3:
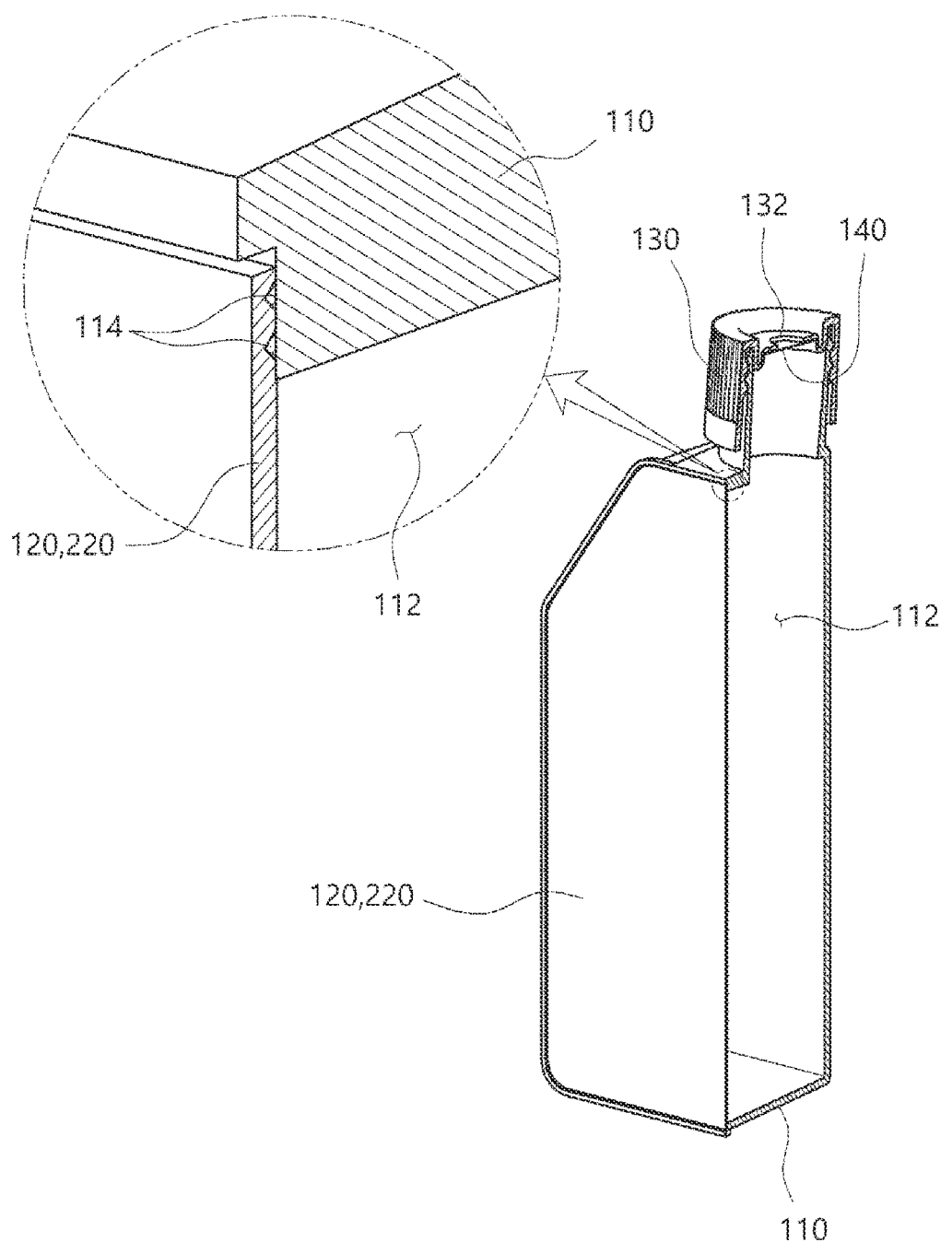
FIG. 3 is a cross-sectional view taken along line A-A of FIG. 1.

As shown in FIGS. 1 to 3, a cell culture device 100 according to an embodiment of the present invention includes a body 110 and a culture plate 120 or 220.

The body 110 may provide a culture space 112 for culturing cells.

For example, the culture space 112 may be formed in the body 110 such that one side thereof is open, as shown in FIG. 2.

To this end, the body 110 may be formed in a box shape with one side open.

One open side of the culture space 112 may be covered by the culture plate 120 or 220.

Accordingly, the culture space 112 may accommodate a predetermined amount of a medium for providing nutrients to the cells during cell culture.

In this case, the body 110 may include an inlet 118 formed to communicate with the culture space 112, and a cap 130 may be detachably coupled to the inlet 118.

Accordingly, even if the open side of the culture space 112 is covered by the culture plate 120 or 220, the medium may be easily injected into the culture space 112 through the inlet 118, and the inlet 118 may be sealed by the cap 130.

In this case, in the cell culture device 100 according to an embodiment of the present invention, the cap 130 may block the movement of liquid such as moisture or medium while allowing gas to flow in and out. For example, the gas may be carbon dioxide required for cell culture.

Accordingly, when cells are cultured in a state in which the medium for cell culture is filled in the culture space 112 in the cell culture device 100 according to an embodiment of the present invention, the medium may be blocked from leaking to the outside from the culture space 112, and foreign substances such as moisture may be blocked from flowing into the culture space 112 from the outside, while gases such as carbon dioxide may be smoothly supplied to the culture space 112.

To this end, a filter member 140 capable of blocking the movement of liquid such as moisture or medium while allowing gas to flow in and out may be provided in the cap 130.

That is, as shown in FIGS. 2 and 3, at least one through hole 132 may be formed in the cap 130, and the filter member 140 may be provided in the cap 130 to cover the through hole 132.

Such a filter member 140 may be any known membrane filter.

As a non-limiting example, the membrane filter may be a nanofiber web in which nanofibers are accumulated in a three-dimensional network structure, but the filter member 140 is not limited thereto, and any of various known materials may be used therefor as long as the materials have waterproofness and air permeability.

Meanwhile, the body 110 may be formed by insert injection molding.

Accordingly, in the cell culture device 100 according to an embodiment of the present invention, since the body 110 may be produced by insert injection molding, mass productivity may be secured and production cost may be reduced.

The culture plate 120 or 220 may be fixed to the body 110 so as to cover one open side of the culture space 112.

To this end, the culture plate 120 or 220 may be provided with a sheet-shaped member having a predetermined area, and an edge of the culture plate 120 or 220 may be fixed to the open edge of the body 110.

For example, the culture plate 120 or 220 may be joined to the open edge of the body 110 through fusion using ultrasonic waves, heat, high frequency, or the like.

To this end, as shown in FIG. 2, at least one fusion mount 114 protruding outward at a certain height along the open edge of the body 110 may be formed on the open edge of the body 110.

The fusion mount 114 may be melted when the body 110 and the culture plate 120 or 220 are fused. Accordingly, the fusion mount 114 may prevent a gap from occurring between the body 110 and the culture plate 120 or 220 while increasing the bonding force between the body 110 and the culture plate 120 or 220.

However, the fixing method of the body 110 and the culture plate 120 or 220 is not limited to the fusion method, and the culture plate 120 or 220 may be attached to the open edge of the body 110 via an adhesive layer. Any of various known methods may be applied as long as they may seal the open lower portion of the culture space 112 while fixing the body 110 and the culture plate 120 or 220 to each other.

Meanwhile, the culture plate 120 or 220 may cover the open side of the culture space 112, and a portion covering the open side of the culture space 112 may form a culture surface. In addition, in the culture plate 120 or 220, the portion forming the culture surface may have a surface modified so that cells may smoothly adhere thereto.

That is, in the cell culture device 100 according to an embodiment of the present invention, the culture plate 120 or 220 covering one open side of the culture space 112 to form a culture surface may be fixed to the open edge of the body 110 in a surface-modified state. Accordingly, during the seeding operation, cells to be cultured may smoothly adhere to one surface of the culture plate 120 or 220, which is the culture surface.

As such, in the case of cell culture using the cell culture device 100 according to an embodiment of the present invention, when a medium containing cells to be cultured is injected into the culture space 112, the cells contained in the medium may smoothly adhere to one surface of the culture plate 120 or 220 forming the culture surface.

Accordingly, in the case of cell culture using the cell culture device 100 according to an embodiment of the present invention, a series of operations such as coating, drying and washing for smoothly attaching cells to the culture surface as in the conventional art may be omitted.

As a result, in the case of cell culture using the cell culture device 100 according to an embodiment of the present invention, the seeding operation for attaching the cells to the culture surface may be performed very simply, thereby improving the operator's work convenience.

In addition, all preparation work for seeding the cells to be cultured is completed by fixing the sheet-shaped culture plate 120 or 220 having a predetermined area to one side of the body 110 in a state in which the surface modification is completed, and therefore, the cell culture device 100 according to an embodiment of the present invention may maintain mass productivity while increasing the operator's convenience.

Here, the culture plate 120 or 220 may be made of a non-toxic material so that the cells attached through the seeding operation may be smoothly cultured.

Figure 4:
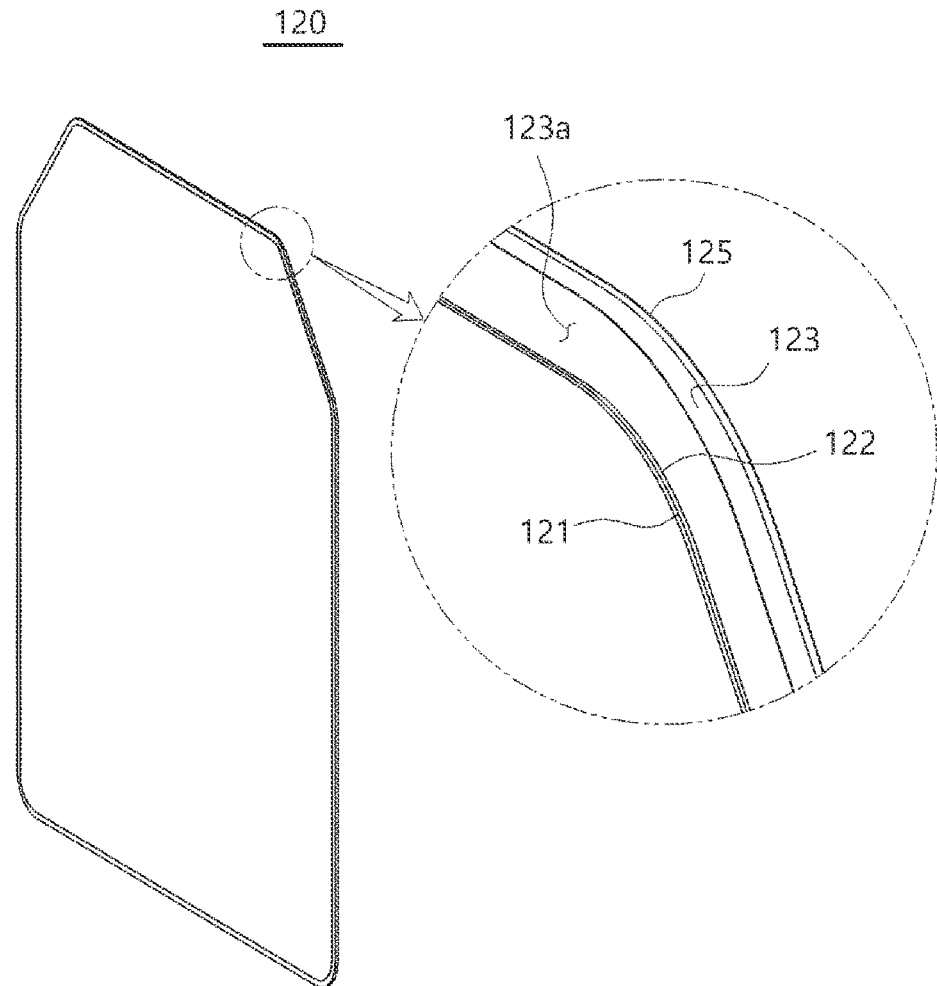
FIG. 4 shows one form of a culture plate that can be applied to a cell culture device according to an embodiment of the present invention.

As an example, as shown in FIG. 4, the culture plate 120 may include a sheet-shaped nanofiber membrane 121 coated with a motif, and a support member 123 attached to one surface of the nanofiber membrane 121 via an adhesive layer 122 so as to support the nanofiber membrane 121.

In this case, the culture plate 120 may be fixed to the open edge of the body 110 so that the nanofiber membrane 121 covers one open side of the culture space 112, and one surface of the nanofiber membrane 121 exposed to the culture space 112 may form a culture surface to which the cells to be cultured adhere.

Accordingly, the cells to be cultured may smoothly adhere to one surface of the nanofiber membrane 121, and the cells adhering to one surface of the nanofiber membrane 121 may be cultured by nutrients supplied from a medium filled in the culture space 112.

In this case, the nanofiber membrane 121 may be attached to one surface of the support member 123 so that an edge of the support member 123 may be directly exposed to the outside.

Figure 5:
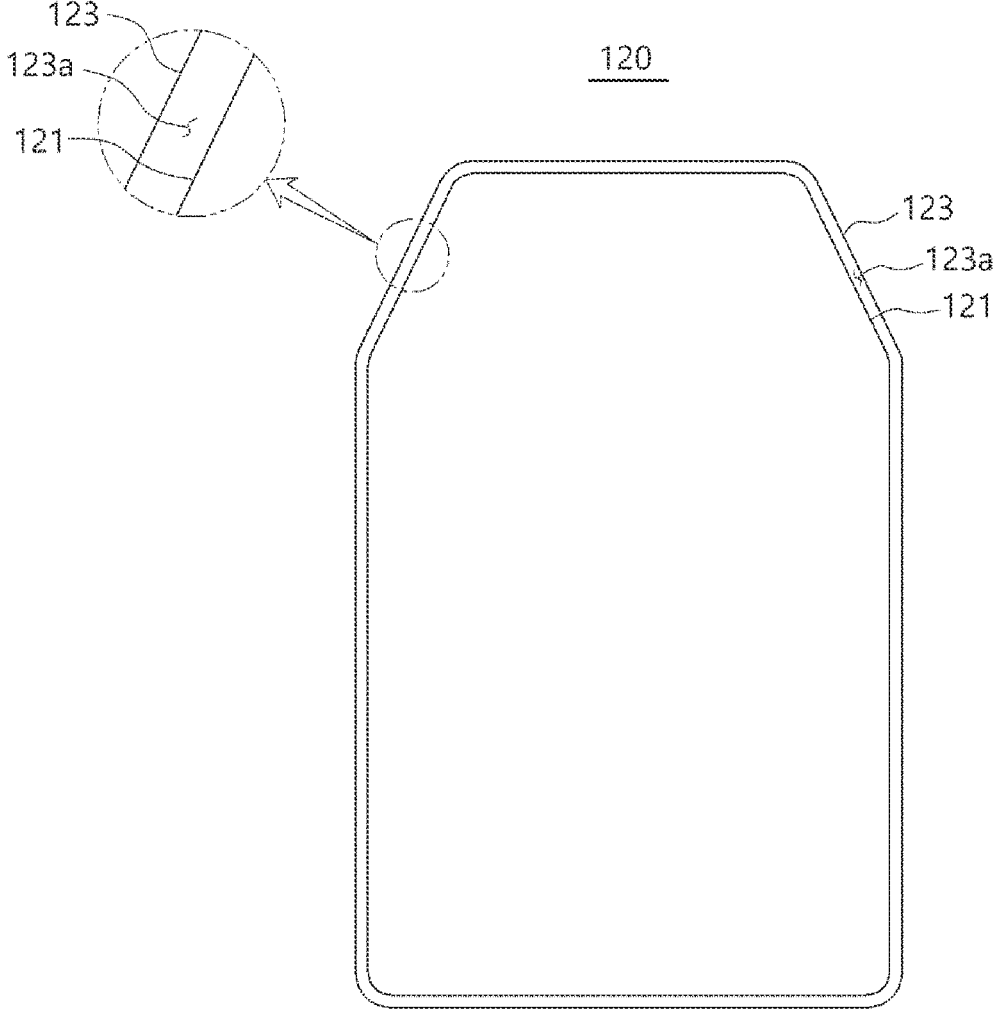
FIG. 5 is a front view of FIG. 4.

To this end, as shown in the enlarged views of FIGS. 4 and 5, the nanofiber membrane 121 may be formed to have a smaller area than the support member 123, and the nanofiber membrane 121 may be attached to one surface of the support member 123 so as to be disposed in an inner region except for an edge of one surface of the support member 123.

Through this, one surface of the support member 123, to which the nanofiber membrane 121 is attached, may include a band-shaped fusion surface 123*a* having a predetermined area while surrounding an edge of the nanofiber membrane 121.

Accordingly, when the culture plate 120 is fixed to the open edge of the body 110, the support member 123 may be in direct contact with the open edge of the body 110 via the fusion surface 123*a*, and all areas of the nanofiber membrane 121 surrounded by the fusion surface 123*a* may be completely accommodated in the culture space 112.

As described above, at least one fusion mount 114 formed on the open edge of the body 110 may directly contact with the support member 123 via the fusion surface 123*a*.

Accordingly, the fusion mount 114 is directly fused to the fusion surface 123*a* of the support member 123 to fix the open edge of the body 110 and the culture plate 120 to each other.

As a result, the bonding force between the culture plate 120 and the body 110 may be increased, and the medium filled in the culture space 112 may be fundamentally blocked from moving along the nanofiber membrane 121 to leak out of the culture space 112.

Figure 6:
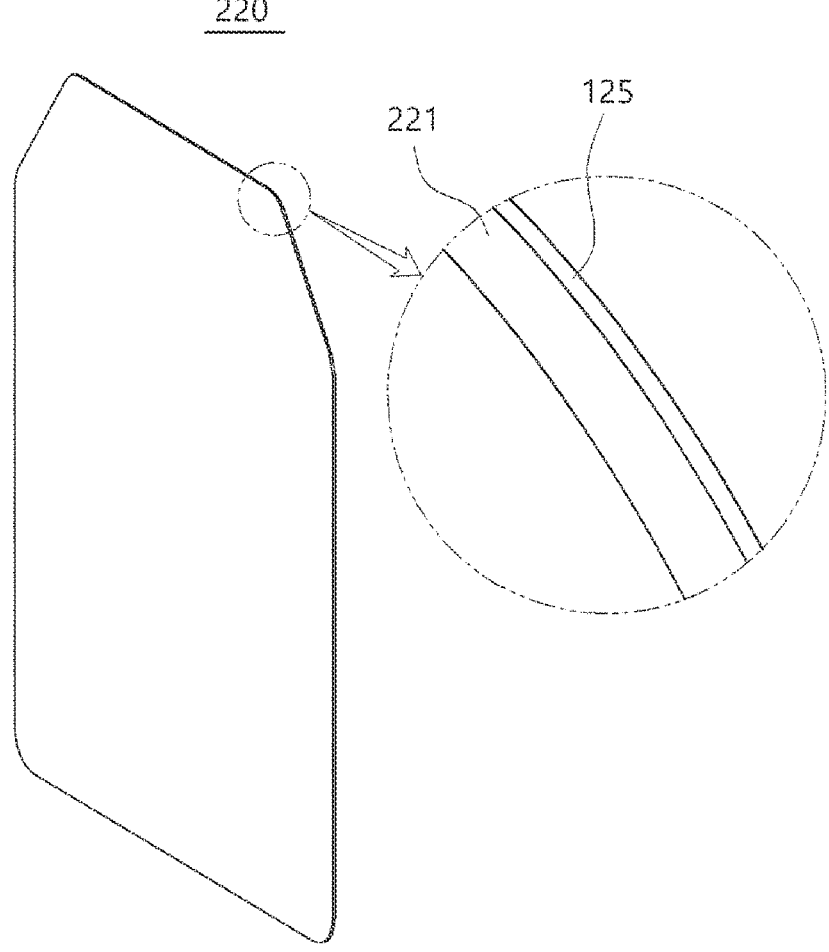
FIG. 6 shows another form of a culture plate that can be applied to a cell culture device according to an embodiment of the present invention.

As another example, as shown in FIG. 6, the culture plate 220 may be a sheet-shaped film member 221 treated with plasma.

Accordingly, the cells to be cultured may smoothly adhere to the surface of the film member 221, and the cells adhering to the surface of the film member 221 may be cultured by nutrients supplied from the medium filled in the culture space 112.

However, the types of the culture plate 120 or 220 are not limited to the above, and any of various known materials used in cell culture may be used as long as it may be formed in a sheet-like shape and easily attach cells thereto.

On the other hand, as shown in the enlarged views of FIGS. 4 and 6, a release film 125 may be laminated on one surface of the culture plate 120 or 220.

Such a release film 125 may remain attached to one surface of the culture plate 120 or 220 during the surface modification of the culture plate 120 or 220, and may be removed from one surface of the culture plate 120 or 220 after the surface modification is completed.

That is, the release film 125 may be attached to one surface of the above-described support member 123 or one surface of the above-described the film member 221.

The release film 125 may cover a portion other than the culture surface, to which cells adhere, during the surface modification process of the nanofiber membrane 121 or the film member 221.

As a result, it is possible to prevent surface modification of unnecessary parts of the culture plate 120 or 220 and to prevent in advance the cleaning liquid used in the process of cleaning the coating liquid from being smeared on one surface of the support member 123.

Meanwhile, in the cell culture device 100 according to an embodiment of the present invention, the body 110, the support member 123 and the film member 221 which may be bonded to each other may be made of the same material.

As a result, in the cell culture device 100 according to an embodiment of the present invention, it is also possible to prevent a decrease in adhesion or bonding strength due to a difference in material.

However, according to embodiments of the present invention, the materials of the body 110, the support member 123, and the film member 221 are not limited to the same material, and may be different from each other.

Although the invention has been illustrated and described in greater detail with reference to the exemplary embodiment, the invention is not limited to the examples disclosed, and further variations can be inferred by a person skilled in the art, without departing from the scope of protection of the invention.

For the sake of clarity, it is to be understood that the use of "a" or "an" throughout this application does not exclude a plurality, and "comprising" does not exclude other steps or elements.

The invention claimed is:

1. A cell culture device comprising:
   a body including a culture space with one open side; and
   a sheet-shaped culture plate fixed to the body to cover the open side of the culture space and forming, on a surface exposed to the culture space, a culture surface on which cells are cultured, the surface of the culture plate forming the culture surface being surface-modified so that cells can smoothly adhere to the culture surface; and
   a release film laminated on an exposed surface of the culture plate opposite to the culture surface;
   wherein the culture plate is fixed to an open rim of the body with the surface modification completed so as to provide the surface-modified culture surface;
   wherein, during a surface-modification treatment of the culture plate, the release film remains attached to the culture plate so that, while the culture surface is surface-modified, the exposed surface remains non-modified, and the release film is thereafter removed.

2. The cell culture device of claim 1, wherein the culture plate includes a sheet-shaped nanofiber membrane coated with a motif, and a support member attached to one surface of the nanofiber membrane via an adhesive layer so as to support the nanofiber membrane, further wherein an exposed surface of the nanofiber membrane forms the culture surface.

3. The cell culture device of claim 2, wherein the culture plate is formed such that the sheet-shaped nanofiber membrane has a smaller area than the support member; and the support member includes a fusion surface formed on one surface to surround an edge of the nanofiber membrane, further wherein the fusion surface is in direct contact with the body and fixed thereto.

4. The cell culture device of claim 3, wherein the body includes at least one fusion mount protruding outward at a certain height along an open edge thereof, and the at least one fusion mount is fused with the fusion surface of the support member to fix the culture plate to the body.

5. The cell culture device of claim 1, wherein the culture plate is a sheet-shaped film member treated with plasma, and one surface of the sheet-shaped film member forms the culture surface.

6. The cell culture device of claim 1, wherein the culture plate is made of a non-toxic material.

7. The cell culture device of claim 1, wherein the cell culture device further includes an inlet formed on one side of the body to communicate with the culture space, and a cap detachably coupled to the inlet.

8. The cell culture device of claim 7, wherein the cap further includes a filter member having waterproofness and breathability.

* * * * *